(12) United States Patent
Plachta et al.

(10) Patent No.: US 11,691,004 B2
(45) Date of Patent: Jul. 4, 2023

(54) DEVICE FOR EXTRAVASAL OR EXTRANEURONAL FASTENING OF A MEDICAL IMPLANT IN THE MANNER OF A COMPRESSION SLEEVE

(71) Applicant: Neuroloop GmbH, Freiburg (DE)

(72) Inventors: Dennis Plachta, Vörstetten (DE); Tim Boretius, Freiburg (DE); Fabian Kimmig, Teningen (DE); Christina Hassler, Reute (DE)

(73) Assignee: NEUROLOOP GMBH, Freiburg (DE)

( * ) Notice: Subject to any disclaimer, the term of this patent is extended or adjusted under 35 U.S.C. 154(b) by 28 days.

(21) Appl. No.: 17/056,345

(22) PCT Filed: May 7, 2019

(86) PCT No.: PCT/EP2019/061599
§ 371 (c)(1),
(2) Date: Nov. 17, 2020

(87) PCT Pub. No.: WO2019/219436
PCT Pub. Date: Nov. 21, 2019

(65) Prior Publication Data
US 2021/0162208 A1    Jun. 3, 2021

(30) Foreign Application Priority Data
May 17, 2018   (DE) .................... 10 2018 207 709.6

(51) Int. Cl.
*A61N 1/05*    (2006.01)

(52) U.S. Cl.
CPC .................................. *A61N 1/0556* (2013.01)

(58) Field of Classification Search
CPC .... A61N 1/3605; A61N 1/0582; A61N 1/0556
See application file for complete search history.

(56) References Cited

U.S. PATENT DOCUMENTS

| | | |
|---|---|---|
| 4,341,221 A | 7/1982 | Testerman |
| 4,602,624 A | 7/1986 | Naples et al. |
| 5,344,438 A | 9/1994 | Testerman et al. |

(Continued)

FOREIGN PATENT DOCUMENTS

| | | |
|---|---|---|
| DE | 1413065 A1 | 10/1994 |
| DE | 4413065 A1 | 10/1994 |

(Continued)

OTHER PUBLICATIONS

International Search Report for PCT/EP2019/061599, dated Jul. 12, 2019; English translation submitted herewith (5 pgs.).

*Primary Examiner* — Alyssa M Alter
(74) *Attorney, Agent, or Firm* — Fitch, Even, Tabin & Flannery LLP

(57) ABSTRACT

A device for the extravasal or extraneuronal fastening of a medical implant has a biocompatible surface substrate including a first substrate portion which is a compression sleeve and a free end portion. By winding the first substrate portion about a spatial axis, the axis is loosely radially covered in at least one layer by the wound first substrate portion. A second substrate portion, which is attached integrally to the first substrate portion which is not wound about the spatial axis, has a connection extending away from the medical implant.

20 Claims, 5 Drawing Sheets

(56) References Cited

U.S. PATENT DOCUMENTS

| | | | |
|---|---|---|---|
| 5,683,403 A * | 11/1997 | Adams | A61N 1/05 |
| | | | 606/151 |
| 5,897,583 A | 4/1999 | Meyer et al. | |
| 5,919,220 A | 7/1999 | Stieglitz et al. | |
| 6,292,703 B1 | 9/2001 | Meier et al. | |
| 2001/0037061 A1 | 11/2001 | Eckmiller et al. | |
| 2003/0040785 A1 | 2/2003 | Maschino et al. | |
| 2008/0103407 A1 | 5/2008 | Bolea et al. | |
| 2010/0070010 A1 | 3/2010 | Simpson | |
| 2014/0188202 A1 * | 7/2014 | Zarembo | A61N 1/0556 |
| | | | 607/118 |

FOREIGN PATENT DOCUMENTS

| | | |
|---|---|---|
| DE | 4433111 A1 | 3/1996 |
| DE | 10020846 A1 | 12/2001 |
| DE | 19847446 B4 | 4/2010 |
| DE | 202007019439 U1 | 9/2012 |
| EP | 0438510 B1 | 8/1996 |
| EP | 2263745 A1 | 12/2010 |
| EP | 2726142 B1 | 5/2014 |
| WO | 99/49934 A1 | 10/1999 |
| WO | 2013/150524 A1 | 10/2013 |
| WO | 2016/055512 A1 | 4/2016 |

\* cited by examiner

DEVICE FOR EXTRAVASAL OR EXTRANEURONAL FASTENING OF A MEDICAL IMPLANT IN THE MANNER OF A COMPRESSION SLEEVE

CROSS REFERENCE TO RELATED APPLICATIONS

Reference is made to PCT/EP2019/061599 filed May 7, 2019, designating the United States, which claims priority to German Application No. 10 2018 207 709.6 filed May 17, 2018, which are incorporated herein by reference in their entirety.

BACKGROUND OF THE INVENTION

Field of the Invention

The invention relates to a device for the extravasal or extraneuronal fastening of a medical implant with a biocompatible substrate having a first substrate portion which is configured as a compression sleeve and has a free end portion, which by winding the first substrate portion about a spatial axis, is loosely radially covered in at least a layer by the wound first substrate portion, and also a second substrate portion, which is attached integrally to the first substrate portion, is not wound about the spatial axis, and is connectable directly or indirectly to a connection structure leading away from the medical implant.

Description of the Prior Art

A medical implant of this type, configured as a compression sleeve for detection as well as application of neuronal electrical signals for permanent or at least long-term positioning along a nerve fiber bundle within the human or animal body is described in WO 2016/055512 A1 and is also shown schematically in FIG. 2. The medical implant 1, made of a biocompatible substrate 2 and configured as a compression sleeve, comprises a first substrate portion 3 which is wound about a spatial axis 5 forming at least one surface substrate winding which radially surrounds a straight cylindrical hollow space H. Attached on the surface substrate surface facing the straight cylindrical hollow space H are electrode surfaces, (not shown in FIG. 2); which come into physical contact with the epineurium of a nerve fiber bundle encompassed by the compression sleeve 1, which is also not shown in FIG. 2. In order to guarantee that on the one hand the medical implant 1 remains as fixed in place along a nerve fiber bundle after appropriate implantation, and on the other hand can follow the natural changes in shape of the nerve fiber bundle or at least is not subject to any significant mechanical resistance, the individual surface substrate windings loosely adjoin each other and in the event of expansion of the nerve fiber bundle, increase the diameter of the encompassed hollow space H through appropriate relative movement.

Through material pre-tensioning applied to the surface substrate 2 in the first substrate portion 3, the surface substrate 2 takes on a predefined winding configuration without the effect of external forces, in which the free portion end 4 is at least loosely radially covered in one layer by the first substrate portion, that is by at least one substrate winding.

Adjoining the wound first substrate portion 3 in one piece, and which is not wound about the spatial axis 5 is a second substrate portion 6, within which electrical leads are connected to the plurality of electrodes coming into contact with the epineurium of the nerve fiber bundle. In the illustrated example embodiment, the also flat second substrate portion 6 comprises a web-like surface portion 6 orientated in parallel to the spatial axis 5, which via an interface S (not illustrated) is an implantable plug connection for example, is connected to a connection structure 7 leading away from the medical implant 1 along which the electrical leads extend to a separate, preferably implantable unit.

In an unstressed state, the mechanical implant 1 lies along a nerve fiber bundle N in accordance with the schematic view in FIG. 3a to uniformly enclose diametrically the first substrate portion 3 to form a compression sleeve. In this state, none or only a minimal mechanical eternal force acts on the nerve fiber bundle N. If, on the other hand, external forces F act on the medical implant 1 which originate, for example, as shown from the body's own movements, deformations of the winding geometry can occur along the first substrate portion 3 configured as a compression sleeve, through which the fastening of the medical implant along the nerve fiber bundle N can no longer be guaranteed, and, on the other hand, a mechanical stress can act on the nerve fiber bundle through the medical implant. Such stress situations are shown in FIGS. 3b) to e). Thus, for example, tensile forces F, which are essentially orientated in parallel to the longitudinal extension of the nerve fiber bundle N, result in a funnel-shaped deformation within the compression sleeve, which on the one hand leads to a constriction E on nerve fiber bundle N, and on the other hand to a widening A, and associated radial extension of the compression sleeve from nerve fiber bundle N, as seen in FIGS. 3b) and c). Constriction E of the nerve fiber bundle N can also occur in the case of a force F, orientated orthogonally to the longitudinal extension of the nerve fiber bundle, acting on the medical implant 1, as shown in the stress situation as illustrated in FIG. 3d). In this case the force F as a tensile force acts transversely to the nerve fiber bundle N. In FIG. 3e) the force acts in the opposite force direction as a thrust force directed onto the nerve fiber bundle N, through which the compression sleeve widens in diameter and tends to become detached from the nerve fiber bundle N.

A cuff electrode in an original form is set out in DE 44 33 111 A1 and has an interdigital surface form, with individual finger portions opening outward depending on external pressure and force exertions.

U.S. Pat. No. 4,602,624 discloses an implantable cuff electrode with a substrate wound into a hollow cylindrical shape having different internal diameters in the axial longitudinal extension. The hollow cylindrical shape is solely maintained by inherent material predetermined pre-tensioning.

WO 2013/150524 A1 discloses an electrode cuff including a series of individual metal cuffs serving as electrodes, which are all radially encompassed from outside by a metal housing, which can be transformed from an open into a closed state in which the latter is secured by a locking clip mechanism.

SUMMARY OF THE INVENTION

The invention is a device for extravasal or extraneuronal fastening of a medical implant with a biocompatible substrate having a first substrate portion, which is configured as a compression sleeve and has a free end portion, which by winding the first substrate portion about a spatial axis, is loosely radially covered in at least one layer by the wound first substrate portion, and also has a second substrate portion, which is attached integrally to the first substrate portion, which is not wound about the spatial axis, and is connectable directly or indirectly to a connection structure leading away from the medical implant. Thus a secure end at the same time a protected and durable application of the medical implant along an intracorporeal vessel or nerve fiber bundle is obtained. These efforts should avoid movement-related deformations of the compression sleeve, or at least reduce them to such a degree that no appreciable mechanical stresses are exerted on the intracorporeal vessel of nerve fiber bundle. For the operator, these measures should not require appreciable additional effort in terms of time or manipulation during the implantation.

In accordance with the invention, a device for the extravasal or extraneuronal fastening of a medical implant with a biocompatible substrate having a first substrate portion, configured as a compression sleeve. In the region of the end portion of the first substrate portion configured as a compression sleeve, at least one attachment is applied thereto, which in the wound state of the first substrate portion about the spatial axis forms a joint connection between at least one of the first substrate portion and the second substrate portion which are spatially separated from the portion end.

According to the invention, the end at the free portion of the first substrate portion which is configured as a compression sleeve, is detachably firmly connected which by the attachment transmits at least one tensile force to an area of the carrier substrate which is preferably located within the second substrate area, in the area of the carrier substrate that integrally adjoins the first substrate portion of the compression sleeve. The at least one attachment is arranged and designed so that in the case of an external force acting on the medical implant, a stopping or supporting force is produced through which the form and shape of the compression sleeve remains unchanged. The at least one attachment can primarily transmit tensile force between the free portion end and the joint connection area. In principle it is also possible to provide a joint connection area within the first substrate portion, but in this case it must be ensured that between the area of the portion end on which the attachment is applied, and the joint connection at least one complete winding of the first substrate portion extends about the spatial axis.

In a preferred embodiment, the at least one attachment is a flexible and non-stretchable strand of material, preferably a thread or strip. In each case, the strand of material is firmly attached by its two ends in the region of the end of the first substrate portion or is integrally connected thereto. The other end of the strand of material is fastened in the area of at least one of the first and second substrate portion by a detachable firm joint connection, preferably as at least one of a frictional and interlocking connection. Advantageously, for this, in the area of at least one of the first and second substrate portion, the biocompatible substrate has at least one fastening opening completely passing through the substrate, through which the strand of material can be threaded for providing a detachable firm connection, preferably for forming a knot.

In a preferred embodiment, the at least one attachment is a tab which laterally projects beyond the first substrate portion in the area of the end of the portion and is connected thereto in one piece. Provided along the first or second substrate portion is a slit recess into which the tab can be introduced, forming at least one of a frictional and interlocking joint connection. Here, preferably the slit recess is located within an area of the first or second substrate portion which projects beyond the first substrate portion configured as a compression sleeve in the longitudinal extension of the winding. A more detailed explanation of this is set out in the following description with reference to an example embodiment.

Fundamentally, the first substrate portion has a longitudinal winding extension orientated about the spatial axis as well as a longitudinal cuff extension orientated axially to the spatial axis, wherein the longitudinal winding extension is determined by the distance between the free end first portion and the second substrate portion adjoining the first substrate portion. In a preferred embodiment, the longitudinal cuff extension tapers within the first substrate portion as the distance increases to the end of the portion in a stepwise manner, preferably evenly along the winding extension. Through this, the opposite ends of the portion end in the wound form of the first substrate portion axially remain freely accessible from outside, so that the strand of material can extent to the joint connection area without being hindered by each of the opposite ends of the portion end.

BRIEF DESCRIPTION OF THE DRAWINGS

Other aspects and features in accordance with the invention are set out in the further description with reference to the drawings.

As an example, the invention will be described below, without restricting the general inventive concept, by way of examples of embodiment with reference to the drawings. Here.

DETAILED DESCRIPTION OF THE INVENTION

Figure 1A:
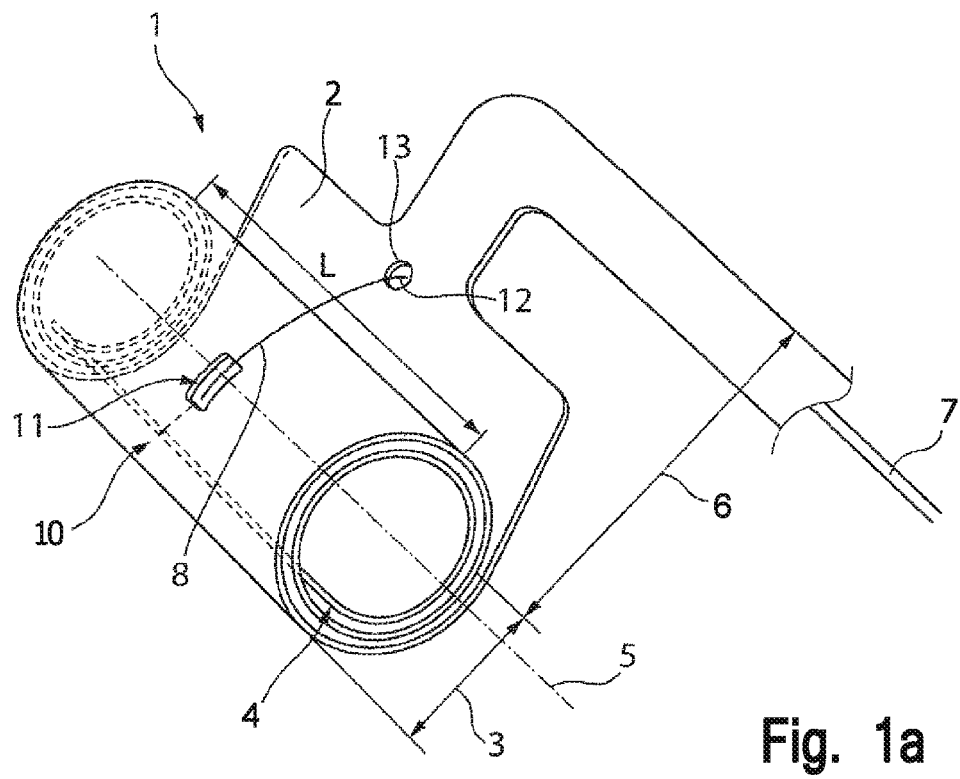
FIG. 1a) shows an example of an embodiment according to the invention with a single connection.

FIG. 1a shows a medical implant 1 with a substrate 2. The first substrate portion 3 forms a compression sleeve, that is the free portion end 4 of the first substrate portion 3 which is wound about the spatial axis 5 forming at least one winding. In FIG. 1a) two one half windings are produced. A second, substrate portion 6, which is not wound integrally, adjoins the first substrate portion 3.

Firmly fastened centrally along the free portion end 4 is one end of a strand of material 8, which preferably is a thread, strip or comparable attachment that transits tensile forces. The firm connection 10 is at least one of bonded/frictional and interlocking non-detachable connection. Starting from the place of connection 10, the strand of material 8 extends through openings 11 which are provided in the first substrate portion 3 and are shown in a wound state, which radially overlap each other in a congruent manner. In this way the strand of material 8 traverses the compression sleeve from inside to outside. The end of the stand of material opposite the connection 10 is locally connected to the second substrate portion 6 formed as a detachable firm joint connection 12. In the area of the joint connection 12, on the surface substrate 2, an opening 13 is provided through which the strand of material 8 passes and, preferably by use of knotting, is connected to the second substrate portion 6.

Figure 3:
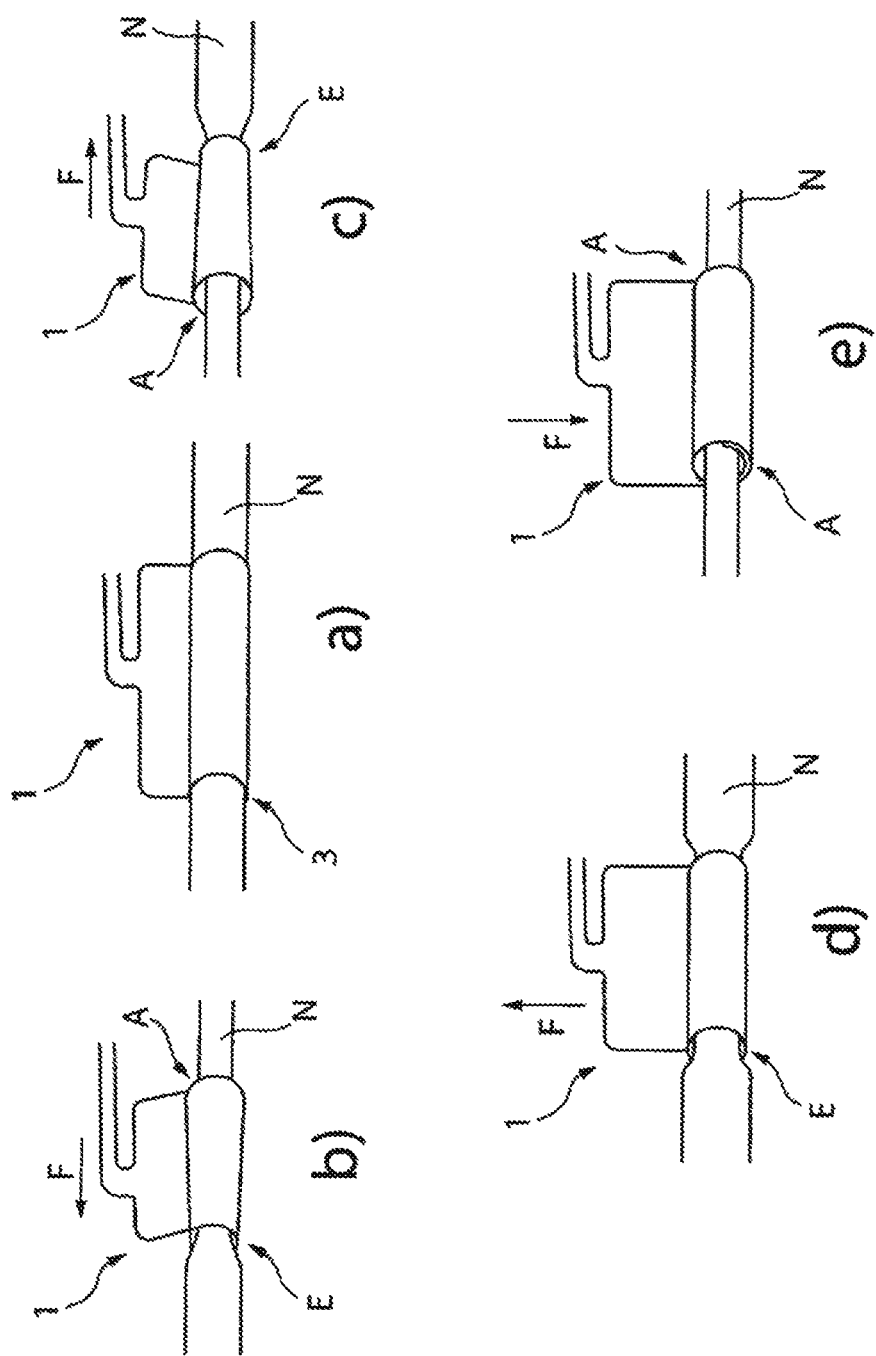
FIG. 3a)-e) show various stress states of a medical implant formed as a compression sleeve.

Through the central application along the longitudinal cuff extension L of the strand material 8 on portion end 4, tensile forces are symmetrically transferred to the portion end 4 with unrolling of the compression sleeve being prevented. In addition, through the symmetrical force transmission, asymmetrical stress conditions, as illustrated in FIGS. 3b) and c), are avoided.

Figure 1B:
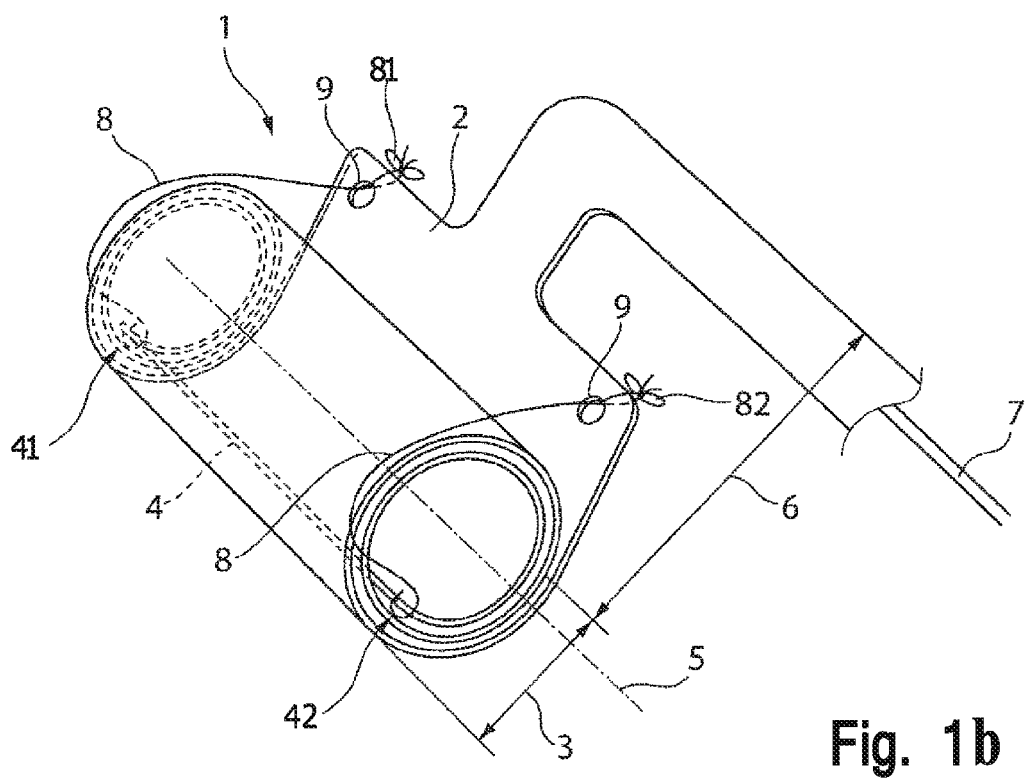
FIG. 1b), c) show examples of an embodiment of the invention each with two connections.

Instead of a single strand of material, the embodiment illustrated in FIG. 1b has two separate strands of material 8 which each are a surgical thread, which are unilaterally firmed fixed to the ends 41, 42 of the free portion end 4 of the first substrate portion 3. At the free ends 81, 82, both strands of material 8 are attached to the second substrate portion 6 via a detachably fixed joint connections 9. In this case also, the joint connections 9, are formed by each passing through the surface substrate 2 in the second substrate portion 6.

Figure 1C:
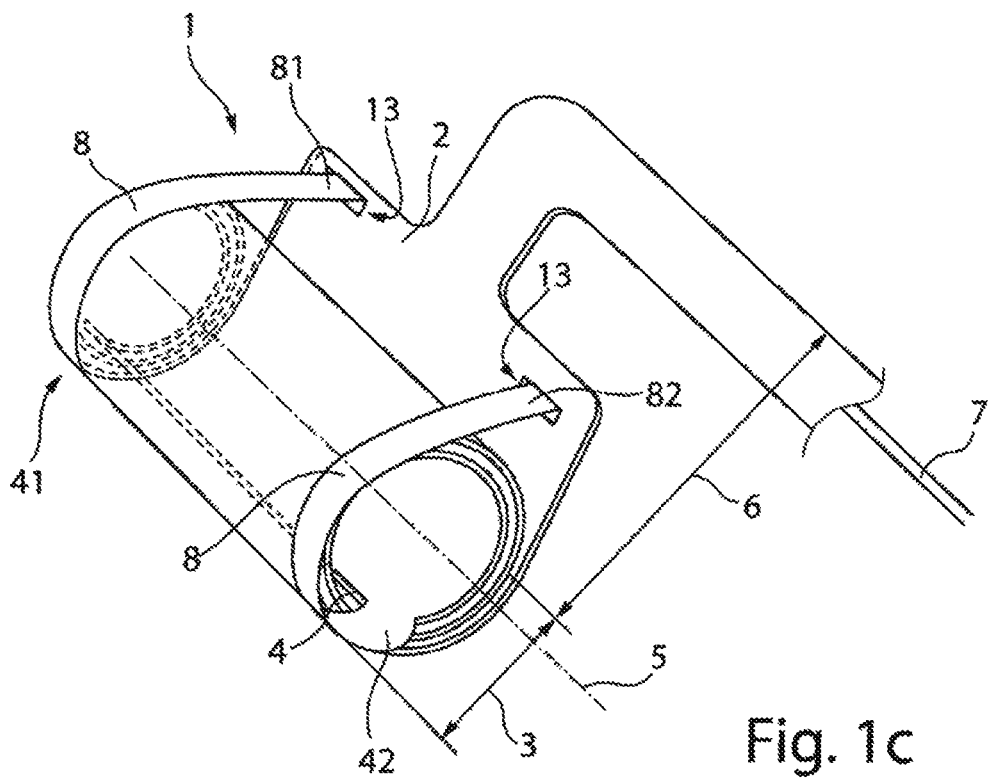
Figure 2:
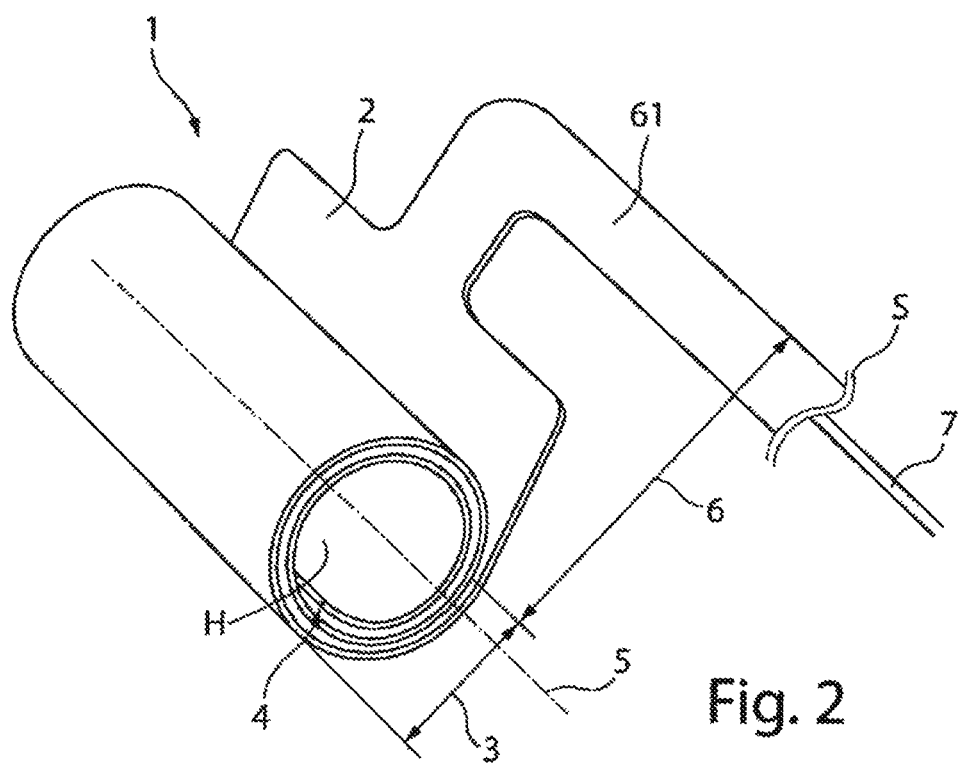
FIG. 2) shows a medical implant with a compression sleeve in accordance with prior art.

FIG. 1c) illustrates an embodiment, which instead of two threads of materials, has two strands of material 8 which are each integrally connected on the ends 41, 42 of the free end 2 portion of the first substrate portion 3. The opposite strip ends 81, 82 extend into corresponding slit recesses 13 within the surface substrate 2 of the second substrate portion 6 and are firmly connected thereto in a detachable manner.

Figure 4A:
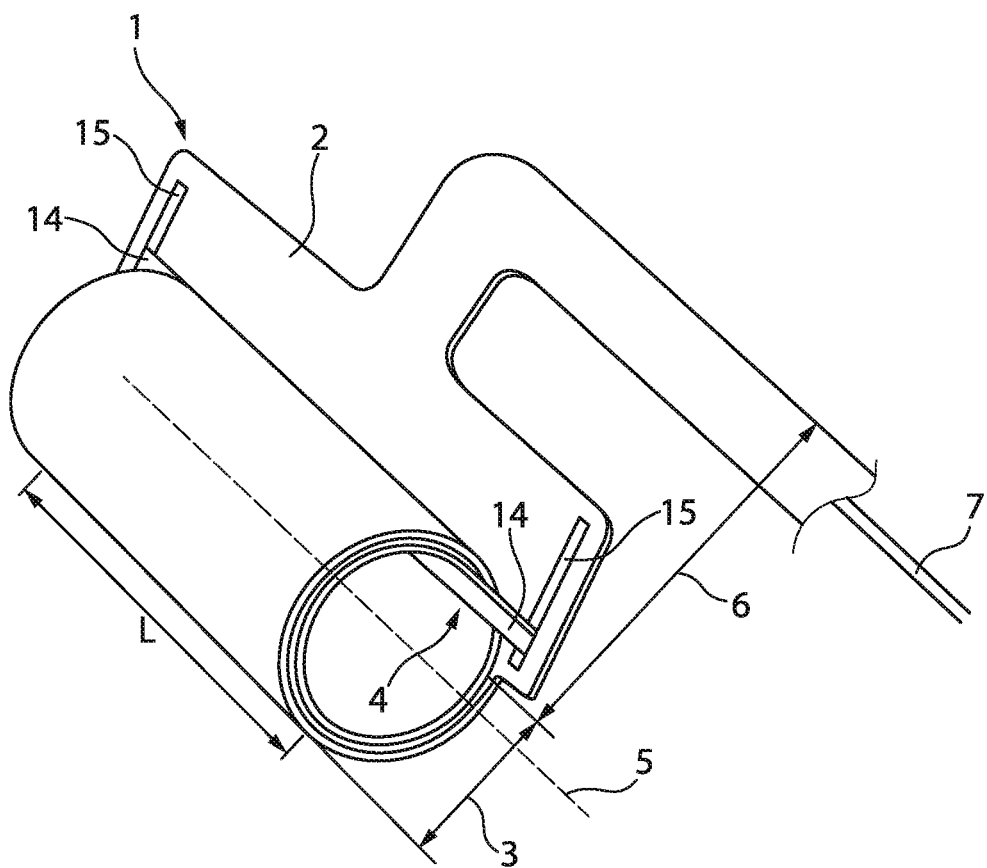
FIG. 4a)-b) shows an example of a embodiment according to the invention with bilateral tab fastening.
Figure 4B:
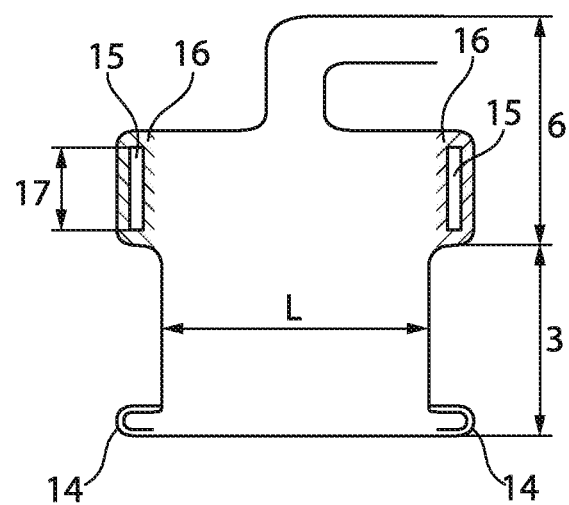

FIGS. 4a and b respectively show a perspective oblique view of a medical implant 1, as well as a view from above in an unwound state. The portion end 4 of the first substrate portion 3 comprises two tabs 14, which laterally project beyond the first substrate portion 3, in the wound state of the first substrate portion 3 which extend into slit recesses 15 on the second substrate portion 6, forming a detachable fixed frictional and interlocking connection. The slit-shaped recesses 15 are located in respective lateral hatched areas 16 of the second substrate portion 6, which on both sides project beyond the longitudinal cuff extension L. The tabs 14, which engage the slit-shaped recesses 5, like the thread-like or strip-shaped strand material 8, prevent uncontrolled loosening of the compression sleeve from a nerve fiber bundle. At the same time, the slit recesses 15 have a slit length 17 which in comparison with the tab width is dimensioned to be slightly larger so that the tabs 14 are moveable to a limited extend along the slit-shaped recesses 15 and the compression sleeve can follow at least one of the natural deformations and expansions of a nerve fiber bundle.

Figure 5A:
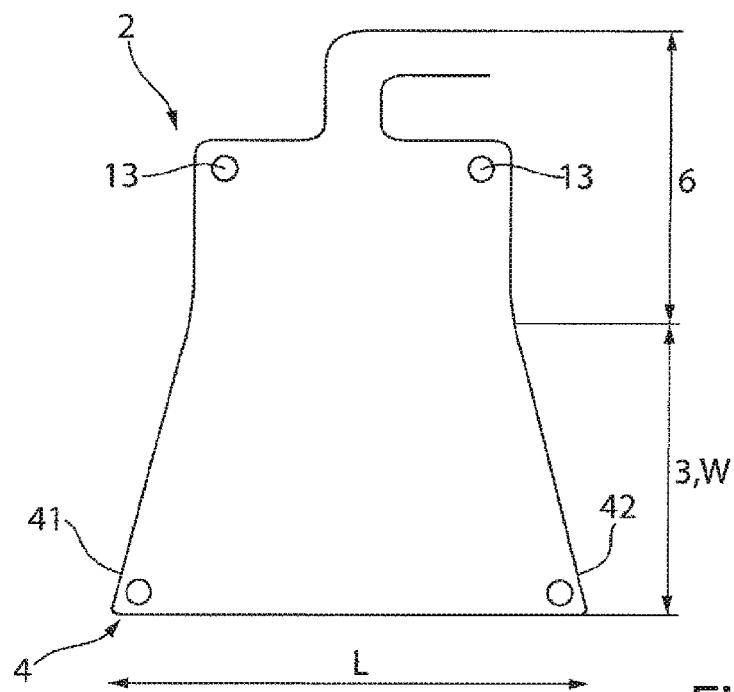
FIG. 5a), b) shows an embodiment of the invention with bilateral freely accessible end areas along the free portion end.
Figure 5B:
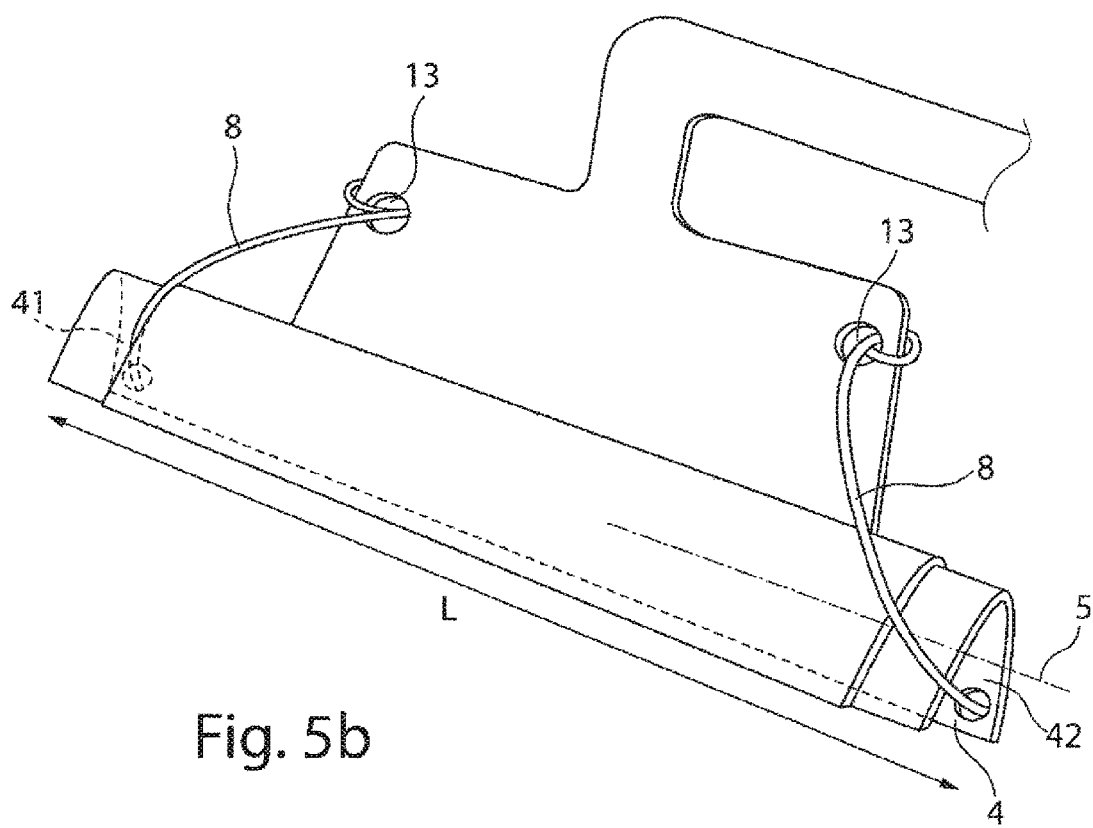

FIGS. 5a), b) show an alternative example of embodiment for forming the fastening provisions according to the invention. FIG. 5a) shows a view from above of the substrate 2 of the compression sleeve in the unwound state and FIG. 5b) show a perspective view of the medical implant in the form of a compression sleeve. The first substrate portion 3 is configured as a trapezoide so that the longitudinal cuff extension L within the first substrate portion 3 tapers evenly along the winding extension W with increasing distance to the area of end portion 4. See the view from above of the unwound surface substrate 3 in accordance with FIG. 5a). By winding the first substrate portion 3 about the spatial axis 5, the ends 41, 42 of the free end portion 4 of the first substrate portion 3 each project laterally outwardly in a freely accessible manner. See the perspective oblique view shown in FIG. 5b). In this way the thread or strip strand materials 8 can be firmly joined to the ends 41, 42 in an uncomplicated manner. The opposite ends of the strand materials 8 are, like in the aforementioned example embodiments, detachably firmly fixed in the area of the second substrate portion 6. Openings 13, through which the end sections of the strand materials 8 pass, can be knotted.

It is of course possible combine the measures described in the above examples of embodiment with each other.

LIST OF REFERENCE NUMBERS

1 Medical implant
2 Biocompatible substrate
3 First substrate portion
4 Free portion end
41, 42 Ends of the portion end
5 Spatial axis
6 Second substrate portion
61 Surface portion formed in a web
7 Connecting structure
8 Strand material
9 Joint connection
10 Connection
11 Opening
12 Joint connection
13 Opening
14 Tab
15 Slit recess
16 Lateral area
17 Length of the slit recess
S Interface
H Cylindrical hollow space
E Constriction
A Widening
W Winding extension
L Longitudinal cuff extension
N Nerve fiber bundle
F External force

The invention claimed is:

1. A device configured for extravasal or extraneuronal fastening of a medical implant into a patient comprising:
a biocompatible substrate comprising means for resisting tensile and compression forces from being applied to the nerve bundle after implantation including a first substrate portion configured by winding the biocompatible substrate at least once completely around a spatial axis to form a compression sleeve and having a free end, the free end as a result of the winding of the first substrate portion around the spatial axis radially covers the at least one wound layer of the first substrate portion, and a second substrate portion which is attached integrally to the first substrate portion which is not wound around the spatial axis, and extends away from the medical implant, and:
a region of the free end when implanted into the patient comprises at least one means, when the first substrate portion is wound around the spatial axis, for providing at least one joint connection between at least one of the first substrate portion and the second substrate portion.

2. The device according to claim 1, wherein:
when the first substrate portion when wound at the free end is applied to an area of the first substrate portion extending at least once around the spatial axis.

3. The device according to claim 2, wherein:
the at least one joint connection is fixed.

4. The device according to claim 3, wherein:
the at least one joint connection is at least one of being frictional and interlocking.

5. The device according to claim 2, wherein:
the at least one joint connection is at least one of being frictional and interlocking.

6. The device according to claim 2, wherein:
the at least one joint connection is a strand of material which transmits tensile forces and is attached to the free end.

7. The device according to claim 2, wherein:
the biocompatible substrate includes at least one fastening opening extending completely through the biocompatible substrate through which the at least one joint connection passes to form the at least one joint connection with at least one of the first and second substrate portions.

8. The device according to claim 1, wherein:
the at least one joint connection is fixed.

9. The device according to claim 8, wherein:
the at least one joint connection is at least one of being frictional and interlocking.

10. The device according to claim 8, wherein:
the at least one joint connection is a strand of material transmitting which transmits tensile forces and is attached to the free end.

11. The device according to claim 8, wherein:
the biocompatible substrate includes at least one fastening opening extending completely through the biocompatible substrate through which the at least one joint connection passes to form the at least one joint connection with at least one of the first and the second substrate portions.

12. The device according to claim 1, wherein:
the at least one joint connection is at least one of being frictional and interlocking.

13. The device according to claim 12, wherein:
the at least one joint connection is a strand of material transmitting tensile forces and is attached to the free end.

14. The device according to claim 12, wherein:
the biocompatible substrate includes at least one fastening opening extending completely through the biocompatible substrate through which the at least one joint connection passes to form the at least one joint connection with at least one of the first and the second substrate portions.

15. The device according to claim 1, wherein:
the at least one joint connection is a strand of material which transmits tensile forces and is attached to the free end.

16. The device according to claim 15, wherein:
the biocompatible substrate includes at least one fastening opening extending completely through the biocompatible substrate, through which the joint connection passes to form the joint connection with at least one of first and the second substrate portions.

17. The device according to claim 1, wherein:
the biocompatible substrate includes at least one fastening opening extending completely through the biocompatible substrate and through which the at least one joint connection passes to form the at least one joint connection with at least one of the first and second substrate portions.

18. The device according to claim 1, comprising:
at least one tab which laterally projects beyond the first substrate portion into at least one slit recess of at least one of the first and the second substrate portions which permits the tab to be introduced into the at least one slit recess to form the joint connection with at least one of the first and second substrate portions.

19. The device according to claim 1, comprising:
the first substrate portion includes an extension orientated around the spatial axis and a longitudinal cuff extension orientated axially relative to a spatial direction of the spatial axis and the longitudinal cuff extension within the first substrate portion tapers either in steps or evenly along the extension of the winding as distance increases from a region of the end of the first substrate portion.

20. The device according to claim 1, comprising:
an end of the first substrate portion comprises two opposite areas at the end to which the at least one joint connection as applied and which opposite areas are along the spatial axis of the at least one of the first substrate portion and the second substrate portion.

* * * * *